(12) United States Patent
McCormick et al.

(10) Patent No.: US 9,724,139 B2
(45) Date of Patent: Aug. 8, 2017

(54) HAMMER TOE IMPLANT AND METHOD

(71) Applicant: Wright Medical Technology, Inc., Arlington, TN (US)

(72) Inventors: Daniel Francis McCormick, Memphis, TN (US); Jessica Lauren Shemwell, Drummonds, TN (US)

(73) Assignee: Wright Medical Technology, Inc., Memphis, TN (US)

( * ) Notice: Subject to any disclaimer, the term of this patent is extended or adjusted under 35 U.S.C. 154(b) by 463 days.

(21) Appl. No.: 14/043,105

(22) Filed: Oct. 1, 2013

(65) Prior Publication Data
US 2015/0094778 A1    Apr. 2, 2015

(51) Int. Cl.
A61F 2/42 (2006.01)
A61B 17/86 (2006.01)
A61B 17/72 (2006.01)

(52) U.S. Cl.
CPC ............ *A61B 17/7291* (2013.01); *A61F 2/42* (2013.01); *A61F 2/4225* (2013.01)

(58) Field of Classification Search
CPC ........................................ A61B 17/86–17/869
See application file for complete search history.

(56) References Cited

U.S. PATENT DOCUMENTS

| 232,369 A | * | 9/1880 | Rukenbrod | ............. | F16B 39/06 411/220 |
|---|---|---|---|---|---|
| 321,389 A | | 6/1885 | Schirmer | | |
| 346,148 A | | 7/1886 | Durham | | |
| 348,589 A | | 9/1886 | Sloan | | |
| 373,074 A | | 11/1887 | Jones | | |
| 430,236 A | | 6/1890 | Rogers | | |
| 561,968 A | | 6/1896 | Coulon | | |
| 736,121 A | | 8/1903 | Lipscomb | | |
| 821,025 A | | 5/1906 | Davies | | |
| 882,937 A | | 3/1908 | Pegley | | |
| 1,966,835 A | | 7/1934 | Stites | | |
| 2,140,749 A | | 12/1938 | Kaplan | | |
| 2,361,107 A | | 10/1944 | Johnson | | |
| 2,451,747 A | | 10/1948 | Kindt | | |
| 2,490,364 A | | 12/1949 | Livingston | | |
| 2,600,517 A | | 6/1952 | Rushing | | |
| 2,697,370 A | | 12/1954 | Brooks | | |
| 2,832,245 A | | 4/1958 | Burrows | | |

(Continued)

FOREIGN PATENT DOCUMENTS

| CN | 102405031 A | 4/2012 |
|---|---|---|
| EP | 0340159 | 11/1989 |

(Continued)

OTHER PUBLICATIONS

European Search Report issued for European patent application No. EP14187111, Jan. 29, 2015, 4 pages.

(Continued)

*Primary Examiner* — Zade Coley
(74) *Attorney, Agent, or Firm* — Duane Morris LLP

(57) ABSTRACT

An implant includes an elongate threaded portion defining a first central longitudinal axis and a groove. The groove defines a second longitudinal central axis that extends in the same direction as the first central longitudinal axis. A blade portion extends from the elongate threaded portion and has a taper terminating at a point.

19 Claims, 9 Drawing Sheets

(56) References Cited

U.S. PATENT DOCUMENTS

| | | |
|---|---|---|
| 2,895,368 A | 7/1959 | Place |
| 2,909,372 A * | 10/1959 | Neri ............... F42B 6/08 473/584 |
| 3,462,765 A | 8/1969 | Swanson |
| 3,466,669 A * | 9/1969 | Flatt ............... A61F 2/4241 623/21.17 |
| 3,593,342 A | 7/1971 | Niebauer et al. |
| 3,681,786 A * | 8/1972 | Lynch ............... A61F 2/18 128/DIG. 21 |
| 3,739,403 A | 6/1973 | Nicolle |
| 3,759,257 A | 9/1973 | Fischer et al. |
| 3,760,802 A | 9/1973 | Fischer et al. |
| 3,779,239 A | 12/1973 | Fischer et al. |
| 3,824,631 A | 7/1974 | Burstein et al. |
| D243,716 S | 3/1977 | Treace et al. |
| 4,047,524 A | 9/1977 | Hall |
| 4,096,896 A | 6/1978 | Engel |
| 4,156,296 A | 5/1979 | Johnson et al. |
| 4,170,990 A | 10/1979 | Baumgart et al. |
| 4,175,555 A | 11/1979 | Herbert |
| 4,198,713 A | 4/1980 | Swanson |
| 4,204,284 A * | 5/1980 | Koeneman ............ A61F 2/4241 403/224 |
| 4,213,208 A * | 7/1980 | Marne ............... A61F 2/4225 623/21.16 |
| 4,237,875 A | 12/1980 | Termanini |
| 4,262,665 A | 4/1981 | Roalstad et al. |
| 4,263,903 A | 4/1981 | Griggs |
| 4,275,717 A | 6/1981 | Bolesky |
| 4,276,660 A * | 7/1981 | Laure ............... A61F 2/4241 623/21.16 |
| 4,278,091 A | 7/1981 | Borzone |
| 4,304,011 A | 12/1981 | Whelan, III |
| 4,321,002 A | 3/1982 | Froehlich |
| 4,364,382 A | 12/1982 | Mennen |
| 4,367,562 A | 1/1983 | Gauthier |
| 4,404,874 A | 9/1983 | Lieser |
| 4,434,796 A | 3/1984 | Karapetian et al. |
| 4,454,875 A | 6/1984 | Pratt et al. |
| 4,485,816 A | 12/1984 | Krumme |
| D277,509 S | 2/1985 | Lawrence et al. |
| D277,784 S | 2/1985 | Sgariato et al. |
| 4,516,569 A | 5/1985 | Evans et al. |
| 4,570,623 A | 2/1986 | Ellison et al. |
| 4,590,928 A | 5/1986 | Hunt et al. |
| D284,099 S | 6/1986 | Laporta et al. |
| 4,634,382 A | 1/1987 | Kusano et al. |
| 4,642,122 A * | 2/1987 | Steffee ............. A61F 2/4225 623/21.19 |
| 4,655,661 A | 4/1987 | Brandt |
| D291,731 S | 9/1987 | Alkins |
| 4,723,540 A | 2/1988 | Gilmer, Jr. |
| 4,723,541 A | 2/1988 | Reese |
| 4,731,087 A | 3/1988 | Sculco et al. |
| 4,756,711 A | 7/1988 | Mai et al. |
| 4,759,768 A | 7/1988 | Hermann et al. |
| 4,790,304 A | 12/1988 | Rosenberg |
| 4,865,606 A | 9/1989 | Rehder |
| 4,908,031 A | 3/1990 | Frisch |
| 4,915,092 A | 4/1990 | Firica et al. |
| 4,932,974 A | 6/1990 | Pappas et al. |
| 4,940,467 A | 7/1990 | Tronzo |
| 4,955,916 A | 9/1990 | Carignan et al. |
| 4,963,144 A | 10/1990 | Huene |
| 4,969,909 A | 11/1990 | Barouk |
| 5,002,563 A | 3/1991 | Pyka et al. |
| 5,007,932 A | 4/1991 | Bekki et al. |
| 5,011,497 A | 4/1991 | Persson et al. |
| 5,019,079 A | 5/1991 | Ross |
| 5,029,753 A | 7/1991 | Hipon et al. |
| 5,037,440 A | 8/1991 | Koenig |
| 5,046,513 A | 9/1991 | Gatturna et al. |
| 5,047,059 A | 9/1991 | Saffar |
| 5,053,038 A | 10/1991 | Sheehan |
| 5,059,193 A | 10/1991 | Kuslich |
| 5,062,851 A | 11/1991 | Branemark |
| 5,089,009 A | 2/1992 | Green |
| 5,092,896 A | 3/1992 | Meuli et al. |
| 5,108,395 A | 4/1992 | Laurain |
| 5,133,761 A | 7/1992 | Krouskop |
| 5,147,363 A | 9/1992 | Harle |
| 5,171,252 A | 12/1992 | Friedland |
| 5,179,915 A | 1/1993 | Cohen et al. |
| 5,190,546 A | 3/1993 | Jervis |
| 5,199,839 A | 4/1993 | DeHaitre |
| 5,207,712 A | 5/1993 | Cohen |
| 5,209,756 A | 5/1993 | Seedhom et al. |
| 5,213,347 A | 5/1993 | Rulon et al. |
| 5,222,975 A | 6/1993 | Crainich |
| 5,246,443 A | 9/1993 | Mai |
| 5,281,225 A | 1/1994 | Vicenzi |
| 5,304,204 A | 4/1994 | Bregen |
| 5,324,307 A | 6/1994 | Jarrett et al. |
| 5,326,364 A | 7/1994 | Clift, Jr. et al. |
| 5,326,366 A | 7/1994 | Pascarella et al. |
| 5,330,476 A | 7/1994 | Hiot et al. |
| 5,342,396 A | 8/1994 | Cook |
| 5,352,229 A | 10/1994 | Goble et al. |
| 5,354,301 A | 10/1994 | Castellano |
| 5,358,405 A | 10/1994 | Imai |
| 5,360,450 A | 11/1994 | Giannini |
| 5,366,479 A | 11/1994 | McGarry et al. |
| 5,380,334 A | 1/1995 | Torrie et al. |
| 5,395,372 A | 3/1995 | Holt et al. |
| 5,405,400 A | 4/1995 | Linscheid et al. |
| 5,405,401 A | 4/1995 | Lippincott, III et al. |
| 5,417,692 A | 5/1995 | Goble et al. |
| 5,425,776 A | 6/1995 | Cohen |
| 5,425,777 A * | 6/1995 | Sarkisian ............ A61F 2/30767 606/76 |
| 5,437,674 A | 8/1995 | Worcel et al. |
| 5,449,359 A | 9/1995 | Groiso |
| 5,454,814 A | 10/1995 | Comte |
| 5,458,648 A | 10/1995 | Berman et al. |
| 5,470,230 A | 11/1995 | Daftary et al. |
| 5,474,557 A | 12/1995 | Mai |
| 5,480,447 A | 1/1996 | Skiba |
| 5,484,443 A | 1/1996 | Pascarella et al. |
| 5,498,265 A | 3/1996 | Asnis et al. |
| 5,507,822 A | 4/1996 | Bouchon et al. |
| 5,516,248 A | 5/1996 | DeHaitre |
| 5,522,903 A | 6/1996 | Sokolow et al. |
| 5,529,075 A | 6/1996 | Clark |
| 5,536,127 A | 7/1996 | Pennig |
| 5,549,681 A | 8/1996 | Segmüller et al. |
| 5,551,871 A | 9/1996 | Besselink et al. |
| 5,554,157 A | 9/1996 | Errico et al. |
| 5,578,034 A | 11/1996 | Estes |
| 5,591,165 A | 1/1997 | Jackson |
| 5,595,563 A | 1/1997 | Moisdon |
| 5,601,558 A | 2/1997 | Torrie et al. |
| D378,409 S | 3/1997 | Michelson |
| 5,634,925 A | 6/1997 | Urbanski |
| 5,643,264 A | 7/1997 | Sherman et al. |
| 5,645,599 A | 7/1997 | Samani |
| 5,660,188 A | 8/1997 | Groiso |
| 5,669,913 A | 9/1997 | Zobel |
| 5,674,297 A | 10/1997 | Lane et al. |
| 5,683,466 A | 11/1997 | Vitale |
| 5,690,629 A | 11/1997 | Asher et al. |
| 5,702,472 A | 12/1997 | Huebner |
| 5,707,395 A | 1/1998 | Li |
| 5,713,903 A | 2/1998 | Sander et al. |
| 5,713,904 A | 2/1998 | Errico et al. |
| 5,720,753 A | 2/1998 | Sander et al. |
| 5,725,585 A | 3/1998 | Zobel |
| 5,728,127 A | 3/1998 | Asher et al. |
| 5,733,307 A * | 3/1998 | Dinsdale ............ A61B 17/0401 606/104 |
| 5,749,916 A | 5/1998 | Richelsoph |
| 5,769,852 A * | 6/1998 | Brånemark ........ A61B 17/8605 606/314 |
| 5,776,202 A | 7/1998 | Copf et al. |

(56) References Cited

U.S. PATENT DOCUMENTS

| | | |
|---|---|---|
| 5,779,707 A | 7/1998 | Bertholet et al. |
| 5,782,927 A | 7/1998 | Klawittler et al. |
| 5,785,713 A | 7/1998 | Jobe |
| 5,840,078 A | 11/1998 | Yerys |
| 5,853,414 A | 12/1998 | Groiso |
| 5,876,434 A | 3/1999 | Flomenblit et al. |
| 5,882,444 A | 3/1999 | Flomenblit et al. |
| 5,893,850 A | 4/1999 | Cachia |
| 5,919,193 A | 7/1999 | Slavitt |
| 5,928,236 A | 7/1999 | Augagneur et al. |
| 5,941,890 A | 8/1999 | Voegele et al. |
| 5,951,288 A | 9/1999 | Sawa |
| 5,958,159 A | 9/1999 | Prandi |
| 5,980,524 A | 11/1999 | Justin et al. |
| 5,984,970 A | 11/1999 | Bramlet |
| 5,984,971 A | 11/1999 | Faccioli et al. |
| 6,011,497 A | 1/2000 | Tsang et al. |
| 6,017,366 A | 1/2000 | Berman |
| 6,030,162 A | 2/2000 | Huebner |
| 6,045,573 A | 4/2000 | Wenstrom, Jr. et al. |
| 6,048,151 A * | 4/2000 | Kwee .................. F16B 39/06 411/217 |
| 6,048,343 A | 4/2000 | Mathis et al. |
| 6,083,242 A | 7/2000 | Cook |
| 6,099,571 A | 8/2000 | Knapp |
| 6,102,642 A | 8/2000 | Kawashita et al. |
| 6,146,387 A | 11/2000 | Trott et al. |
| 6,187,009 B1 | 2/2001 | Herzog et al. |
| 6,193,757 B1 | 2/2001 | Foley et al. |
| 6,197,037 B1 | 3/2001 | Hair |
| 6,200,321 B1 | 3/2001 | Orbay et al. |
| 6,200,330 B1 | 3/2001 | Benderev et al. |
| 6,200,345 B1 | 3/2001 | Morgan |
| 6,224,600 B1 | 5/2001 | Protogirou |
| 6,248,109 B1 | 6/2001 | Stofella |
| 6,299,613 B1 | 10/2001 | Ogilvie et al. |
| 6,305,053 B1 | 10/2001 | Galbreath |
| 6,306,140 B1 | 10/2001 | Siddiqui |
| 6,319,284 B1 | 11/2001 | Rushdy et al. |
| 6,332,885 B1 | 12/2001 | Martella |
| 6,336,928 B1 | 1/2002 | Guerin et al. |
| 6,352,560 B1 | 3/2002 | Poeschmann et al. |
| 6,383,223 B1 | 5/2002 | Baehler et al. |
| 6,386,877 B1 | 5/2002 | Sutter |
| 6,406,234 B2 | 6/2002 | Frigg |
| 6,413,260 B1 | 7/2002 | Berrevoets et al. |
| 6,419,706 B1 | 7/2002 | Graf |
| 6,423,097 B2 | 7/2002 | Rauscher |
| 6,428,634 B1 | 8/2002 | Besselink et al. |
| 6,436,099 B1 | 8/2002 | Drewry et al. |
| 6,451,057 B1 | 9/2002 | Chen et al. |
| 6,454,808 B1 | 9/2002 | Masada |
| 6,458,134 B1 | 10/2002 | Songer et al. |
| 6,475,242 B1 | 11/2002 | Bramlet |
| 6,508,841 B2 | 1/2003 | Martin et al. |
| 6,517,543 B1 | 2/2003 | Berrevoets et al. |
| 6,533,788 B1 | 3/2003 | Orbay |
| 6,551,321 B1 | 4/2003 | Burkinshaw |
| 6,551,343 B1 | 4/2003 | Tomala et al. |
| 6,575,973 B1 | 6/2003 | Shekalim |
| 6,575,976 B2 | 6/2003 | Grafton |
| 6,582,453 B1 | 6/2003 | Tran et al. |
| 6,648,890 B2 | 11/2003 | Culbert et al. |
| 6,679,668 B2 | 1/2004 | Martin et al. |
| 6,682,565 B1 | 1/2004 | Krishnan |
| 6,685,706 B2 | 2/2004 | Padget et al. |
| 6,699,247 B2 | 3/2004 | Zucherman et al. |
| 6,699,292 B2 | 3/2004 | Ogilvie et al. |
| 6,706,045 B2 | 3/2004 | Lin et al. |
| 6,767,350 B1 | 7/2004 | Lob |
| 6,773,437 B2 | 8/2004 | Ogilvie et al. |
| 6,811,568 B2 | 11/2004 | Minamikawa |
| 6,869,449 B2 | 3/2005 | Ball et al. |
| 6,875,235 B2 | 4/2005 | Ferree |
| 7,037,309 B2 | 5/2006 | Weil et al. |
| 7,037,324 B2 | 5/2006 | Martinek |
| 7,037,342 B2 | 5/2006 | Nilsson et al. |
| 7,041,106 B1 | 5/2006 | Carver et al. |
| 7,044,953 B2 | 5/2006 | Capanni |
| 7,112,214 B2 | 9/2006 | Peterson et al. |
| 7,182,787 B2 | 2/2007 | Hassler et al. |
| 7,192,445 B2 | 3/2007 | Ellingsen et al. |
| 7,207,994 B2 | 4/2007 | Vlahos et al. |
| 7,240,677 B2 | 7/2007 | Fox |
| 7,261,716 B2 * | 8/2007 | Strobel ............. A61B 17/8615 606/232 |
| 7,291,175 B1 | 11/2007 | Gordon |
| 7,569,061 B2 * | 8/2009 | Colleran ............. A61B 17/1735 606/104 |
| 7,585,316 B2 | 9/2009 | Trieu |
| 7,588,603 B2 | 9/2009 | Leonard |
| 7,695,471 B2 | 4/2010 | Cheung et al. |
| 7,708,759 B2 | 5/2010 | Lubbers et al. |
| 7,727,235 B2 | 6/2010 | Contiliano et al. |
| 7,780,701 B1 | 8/2010 | Meridew et al. |
| 7,780,737 B2 | 8/2010 | Bonnard et al. |
| 7,785,357 B2 | 8/2010 | Guan et al. |
| 7,837,738 B2 | 11/2010 | Reigstad et al. |
| 7,842,091 B2 | 11/2010 | Johnstone et al. |
| 7,887,589 B2 | 2/2011 | Glenn et al. |
| 7,909,880 B1 | 3/2011 | Grant |
| 7,918,879 B2 | 4/2011 | Yeung et al. |
| 7,959,681 B2 | 6/2011 | Lavi |
| 7,963,995 B2 | 6/2011 | Richelsoph |
| 7,976,565 B1 | 7/2011 | Meridew |
| 7,985,246 B2 | 7/2011 | Trieu |
| 8,002,811 B2 | 8/2011 | Corradi et al. |
| 8,057,524 B2 | 11/2011 | Meridew |
| 8,100,983 B2 | 1/2012 | Schulte |
| 8,118,839 B2 | 2/2012 | Taylor |
| 8,118,849 B2 | 2/2012 | Wahl et al. |
| 8,197,509 B2 | 6/2012 | Contiliano et al. |
| 8,262,712 B2 | 9/2012 | Coilard-Lavirotte et al. |
| 8,267,939 B2 | 9/2012 | Cipoletti et al. |
| 8,337,537 B2 | 12/2012 | Pelo et al. |
| 8,394,097 B2 | 3/2013 | Peyrot et al. |
| 8,394,132 B2 | 3/2013 | Lewis et al. |
| 8,414,583 B2 | 4/2013 | Prandi et al. |
| 8,465,525 B2 | 6/2013 | Hawkins et al. |
| 8,475,456 B2 | 7/2013 | Augoyard et al. |
| 8,523,944 B2 | 9/2013 | Jimenez et al. |
| 8,591,545 B2 | 11/2013 | Lunn et al. |
| 8,608,785 B2 | 12/2013 | Reed et al. |
| 8,616,091 B2 | 12/2013 | Anderson |
| 8,636,457 B2 | 1/2014 | Connors |
| 8,641,769 B2 | 2/2014 | Malandain |
| 8,647,390 B2 | 2/2014 | Bellemere et al. |
| 8,840,677 B2 | 9/2014 | Kale et al. |
| 8,888,779 B2 * | 11/2014 | Senn ................. A61B 17/725 606/66 |
| D720,072 S | 12/2014 | Cheney et al. |
| 8,906,060 B2 | 12/2014 | Hart |
| 8,986,386 B2 | 3/2015 | Oglaza et al. |
| 8,998,999 B2 | 4/2015 | Lewis et al. |
| 9,044,287 B2 | 6/2015 | Reed et al. |
| 9,056,014 B2 | 6/2015 | McCormick et al. |
| 9,125,704 B2 | 9/2015 | Reed et al. |
| 9,138,274 B1 | 9/2015 | Biesinger et al. |
| 9,149,268 B2 | 10/2015 | Graul et al. |
| 2001/0025199 A1 | 9/2001 | Rauscher |
| 2001/0028836 A1 | 10/2001 | Kohori |
| 2001/0049529 A1 | 12/2001 | Cachia et al. |
| 2002/0019636 A1 | 2/2002 | Ogilvie et al. |
| 2002/0022887 A1 | 2/2002 | Huene |
| 2002/0026194 A1 | 2/2002 | Morrison et al. |
| 2002/0055785 A1 | 5/2002 | Harris |
| 2002/0065561 A1 | 5/2002 | Ogilvie et al. |
| 2002/0068939 A1 | 6/2002 | Levy et al. |
| 2002/0072803 A1 | 6/2002 | Saunders et al. |
| 2002/0082705 A1 | 6/2002 | Bouman et al. |
| 2002/0111690 A1 | 8/2002 | Hyde |
| 2002/0128713 A1 | 9/2002 | Ferree |
| 2002/0165544 A1 | 11/2002 | Perren et al. |
| 2002/0183846 A1 | 12/2002 | Kuslich et al. |

(56) References Cited

U.S. PATENT DOCUMENTS

| | | |
|---|---|---|
| 2003/0032961 A1 | 2/2003 | Pelo et al. |
| 2003/0040805 A1 | 2/2003 | Minamikawa |
| 2003/0069645 A1 | 4/2003 | Ball et al. |
| 2003/0130660 A1 | 7/2003 | Levy et al. |
| 2003/0191422 A1 | 10/2003 | Sossong |
| 2003/0233095 A1 | 12/2003 | Urbanski et al. |
| 2004/0010315 A1 | 1/2004 | Song |
| 2004/0093081 A1 | 5/2004 | Nilsson et al. |
| 2004/0097941 A1 | 5/2004 | Weiner et al. |
| 2004/0102853 A1 | 5/2004 | Boumann et al. |
| 2004/0111117 A1 | 6/2004 | Colleran et al. |
| 2004/0133204 A1 | 7/2004 | Davies |
| 2004/0138756 A1 | 7/2004 | Reeder |
| 2004/0220574 A1 | 11/2004 | Pelo et al. |
| 2004/0220678 A1 | 11/2004 | Chow et al. |
| 2004/0230193 A1 | 11/2004 | Cheung et al. |
| 2004/0230194 A1 | 11/2004 | Urbanski et al. |
| 2004/0230313 A1 | 11/2004 | Saunders |
| 2004/0249461 A1 | 12/2004 | Ferree |
| 2005/0113836 A1 | 5/2005 | Lozier et al. |
| 2005/0119757 A1 | 6/2005 | Hassler et al. |
| 2005/0123672 A1 | 6/2005 | Justin et al. |
| 2005/0124443 A1* | 6/2005 | Summers .................. F42B 6/08 473/583 |
| 2005/0149031 A1 | 7/2005 | Ciccone et al. |
| 2005/0177158 A1 | 8/2005 | Doubler et al. |
| 2005/0187636 A1 | 8/2005 | Graham |
| 2005/0251265 A1 | 11/2005 | Calandruccio et al. |
| 2005/0261768 A1 | 11/2005 | Trieu |
| 2005/0283159 A1 | 12/2005 | Amara |
| 2006/0052725 A1 | 3/2006 | Santilli |
| 2006/0052878 A1 | 3/2006 | Schmieding |
| 2006/0074421 A1 | 4/2006 | Bickley et al. |
| 2006/0074488 A1 | 4/2006 | Abdou |
| 2006/0074492 A1 | 4/2006 | Frey |
| 2006/0084998 A1 | 4/2006 | Levy et al. |
| 2006/0100715 A1 | 5/2006 | De Villiers |
| 2006/0129153 A1* | 6/2006 | Klaue .................... A61B 17/68 606/916 |
| 2006/0149258 A1 | 7/2006 | Sousa |
| 2006/0173462 A1 | 8/2006 | Kay et al. |
| 2006/0200151 A1 | 9/2006 | Ducharme et al. |
| 2006/0229617 A1 | 10/2006 | Meller et al. |
| 2006/0247787 A1 | 11/2006 | Rydell et al. |
| 2007/0038303 A1 | 2/2007 | Myerson et al. |
| 2007/0078518 A1 | 4/2007 | Lavi |
| 2007/0106283 A1 | 5/2007 | Garcia et al. |
| 2007/0123873 A1 | 5/2007 | Czartoski et al. |
| 2007/0123993 A1 | 5/2007 | Hassler et al. |
| 2007/0142920 A1 | 6/2007 | Niemi |
| 2007/0177959 A1 | 8/2007 | Chopp et al. |
| 2007/0185583 A1 | 8/2007 | Branemark |
| 2007/0185584 A1 | 8/2007 | Kaufmann et al. |
| 2007/0198018 A1 | 8/2007 | Biedermann et al. |
| 2007/0213831 A1 | 9/2007 | de Cubber |
| 2007/0239158 A1 | 10/2007 | Trieu et al. |
| 2007/0293866 A1 | 12/2007 | Stoeckel et al. |
| 2008/0039949 A1 | 2/2008 | Meesenburg et al. |
| 2008/0051912 A1 | 2/2008 | Hollawell |
| 2008/0086139 A1 | 4/2008 | Bourke et al. |
| 2008/0132894 A1 | 6/2008 | Coilard-Lavirotte et al. |
| 2008/0132958 A1 | 6/2008 | Pech et al. |
| 2008/0154385 A1 | 6/2008 | Trail et al. |
| 2008/0161919 A1 | 7/2008 | Melkent |
| 2008/0177262 A1 | 7/2008 | Augoyard et al. |
| 2008/0177291 A1 | 7/2008 | Jensen et al. |
| 2008/0177334 A1 | 7/2008 | Stinnette |
| 2008/0195215 A1 | 8/2008 | Morton |
| 2008/0195219 A1 | 8/2008 | Wiley et al. |
| 2008/0221574 A1 | 9/2008 | Cavallazzi |
| 2008/0221697 A1 | 9/2008 | Graser |
| 2008/0221698 A1 | 9/2008 | Berger |
| 2008/0255618 A1 | 10/2008 | Fisher et al. |
| 2008/0269908 A1 | 10/2008 | Warburton |
| 2008/0294204 A1 | 11/2008 | Chirico et al. |
| 2009/0005782 A1 | 1/2009 | Chirico et al. |
| 2009/0012564 A1 | 1/2009 | Chirico et al. |
| 2009/0036893 A1 | 2/2009 | Kartalian et al. |
| 2009/0105770 A1 | 4/2009 | Berrevoets et al. |
| 2009/0149891 A1 | 6/2009 | Lee et al. |
| 2009/0163918 A1 | 6/2009 | Levy et al. |
| 2009/0187219 A1 | 7/2009 | Pachtman et al. |
| 2009/0204158 A1* | 8/2009 | Sweeney ............ A61B 17/7061 606/309 |
| 2009/0210016 A1 | 8/2009 | Champagne et al. |
| 2009/0216282 A1 | 8/2009 | Blake et al. |
| 2009/0254189 A1 | 10/2009 | Scheker |
| 2009/0254190 A1 | 10/2009 | Gannoe et al. |
| 2009/0259316 A1 | 10/2009 | Ginn et al. |
| 2010/0010637 A1 | 1/2010 | Pequignot |
| 2010/0016982 A1 | 1/2010 | Solomons |
| 2010/0023012 A1 | 1/2010 | Voor |
| 2010/0030221 A1 | 2/2010 | Christian et al. |
| 2010/0049244 A1 | 2/2010 | Cohen et al. |
| 2010/0057214 A1 | 3/2010 | Graham et al. |
| 2010/0061825 A1 | 3/2010 | Liu et al. |
| 2010/0069913 A1 | 3/2010 | Chirico |
| 2010/0069970 A1 | 3/2010 | Lewis et al. |
| 2010/0121390 A1 | 5/2010 | Kleinman |
| 2010/0125274 A1 | 5/2010 | Greenhalgh et al. |
| 2010/0131014 A1 | 5/2010 | Peyrot et al. |
| 2010/0131072 A1 | 5/2010 | Schulte |
| 2010/0161068 A1 | 6/2010 | Lindner et al. |
| 2010/0185295 A1 | 7/2010 | Emmanuel |
| 2010/0217325 A1 | 8/2010 | Hochschuler et al. |
| 2010/0249942 A1 | 9/2010 | Goswami et al. |
| 2010/0256639 A1 | 10/2010 | Tyber et al. |
| 2010/0256770 A1 | 10/2010 | Hakansson et al. |
| 2010/0262254 A1 | 10/2010 | Lawrence et al. |
| 2010/0274293 A1 | 10/2010 | Terrill et al. |
| 2010/0286692 A1 | 11/2010 | Greenhalgh et al. |
| 2010/0292799 A1 | 11/2010 | Hansell et al. |
| 2010/0324556 A1 | 12/2010 | Tyber et al. |
| 2010/0331893 A1 | 12/2010 | Geist et al. |
| 2011/0004255 A1 | 1/2011 | Weiner et al. |
| 2011/0004317 A1 | 1/2011 | Hacking et al. |
| 2011/0066190 A1 | 3/2011 | Schaller et al. |
| 2011/0082507 A1 | 4/2011 | Slaue |
| 2011/0082508 A1 | 4/2011 | Reed |
| 2011/0093017 A1 | 4/2011 | Prasad et al. |
| 2011/0093075 A1 | 4/2011 | Duplessis et al. |
| 2011/0093085 A1 | 4/2011 | Morton |
| 2011/0118739 A1 | 5/2011 | Tyber et al. |
| 2011/0144644 A1* | 6/2011 | Prandi .................... A61B 17/68 606/62 |
| 2011/0144766 A1 | 6/2011 | Kale et al. |
| 2011/0208252 A1* | 8/2011 | Erhart ................ A61B 17/1735 606/310 |
| 2011/0257652 A1 | 10/2011 | Roman |
| 2011/0301652 A1* | 12/2011 | Reed .................. A61B 17/7291 606/319 |
| 2011/0301653 A1* | 12/2011 | Reed .................. A61B 17/1604 606/319 |
| 2011/0306975 A1 | 12/2011 | Kaikkonen et al. |
| 2011/0319946 A1 | 12/2011 | Levy et al. |
| 2012/0016428 A1 | 1/2012 | White et al. |
| 2012/0065692 A1 | 3/2012 | Champagne et al. |
| 2012/0065738 A1 | 3/2012 | Schulman |
| 2012/0089197 A1* | 4/2012 | Anderson .......... A61B 17/7233 606/310 |
| 2012/0136448 A1 | 5/2012 | Seifert et al. |
| 2012/0209337 A1 | 8/2012 | Weinstein |
| 2012/0259419 A1 | 10/2012 | Brown et al. |
| 2012/0271362 A1 | 10/2012 | Martineau et al. |
| 2012/0323241 A1 | 12/2012 | McClellan et al. |
| 2013/0030475 A1 | 1/2013 | Weiner et al. |
| 2013/0053975 A1 | 2/2013 | Reed et al. |
| 2013/0060295 A1 | 3/2013 | Reed et al. |
| 2013/0066383 A1 | 3/2013 | Anderson et al. |
| 2013/0066435 A1 | 3/2013 | Averous et al. |
| 2013/0079776 A1 | 3/2013 | Zwirkoski et al. |
| 2013/0090655 A1 | 4/2013 | Tontz |
| 2013/0096634 A1 | 4/2013 | Suh |
| 2013/0123862 A1 | 5/2013 | Anderson et al. |

(56) References Cited

U.S. PATENT DOCUMENTS

| | | |
|---|---|---|
| 2013/0131822 A1 | 5/2013 | Lewis et al. |
| 2013/0150965 A1 | 6/2013 | Taylor et al. |
| 2013/0190761 A1 | 7/2013 | Prandi et al. |
| 2013/0211451 A1 | 8/2013 | Wales et al. |
| 2013/0226191 A1 | 8/2013 | Thoren et al. |
| 2013/0253597 A1 | 9/2013 | Augoyard et al. |
| 2013/0274814 A1 | 10/2013 | Weiner et al. |
| 2013/0317559 A1 | 11/2013 | Leavitts et al. |
| 2013/0325138 A1 | 12/2013 | Graham |
| 2014/0018930 A1 | 1/2014 | Oster |
| 2014/0025125 A1 | 1/2014 | Sack et al. |
| 2014/0052196 A1 | 2/2014 | McGinley et al. |
| 2014/0107713 A1 | 4/2014 | Pech et al. |
| 2014/0135768 A1 | 5/2014 | Roman |
| 2014/0142715 A1 | 5/2014 | McCormick |
| 2014/0180428 A1 | 6/2014 | McCormick |
| 2014/0188179 A1 | 7/2014 | McCormick |
| 2014/0188237 A1 | 7/2014 | McCormick et al. |
| 2014/0188239 A1 | 7/2014 | Cummings |
| 2014/0257289 A1 | 9/2014 | Kecman et al. |
| 2014/0276825 A1 | 9/2014 | Brown et al. |
| 2014/0277185 A1 | 9/2014 | Boileau et al. |
| 2014/0277186 A1 | 9/2014 | Granberry et al. |
| 2015/0012098 A1 | 1/2015 | Eastlack et al. |
| 2015/0018954 A1 | 1/2015 | Loebl et al. |
| 2015/0073413 A1 | 3/2015 | Palmer et al. |
| 2015/0088136 A1 | 3/2015 | Vitek et al. |
| 2015/0088266 A1 | 3/2015 | Sander et al. |
| 2015/0112342 A1 | 4/2015 | Penzimer et al. |
| 2015/0141994 A1 | 5/2015 | Cheney et al. |
| 2015/0142066 A1 | 5/2015 | Shemwell et al. |
| 2015/0164563 A1 | 6/2015 | Lewis et al. |
| 2015/0223849 A1 | 8/2015 | McCormick et al. |
| 2015/0342655 A1 | 12/2015 | Reed et al. |

FOREIGN PATENT DOCUMENTS

| | | |
|---|---|---|
| EP | 0409364 | 1/1991 |
| EP | 0611557 | 8/1994 |
| FR | 736058 | 11/1932 |
| FR | 1036978 | 9/1953 |
| FR | 2605878 | 5/1988 |
| FR | 2645735 | 10/1990 |
| FR | 2651119 | 3/1991 |
| FR | 2783702 | 3/2000 |
| FR | 2787313 | 6/2000 |
| FR | 2794019 | 12/2000 |
| FR | 2801189 A1 | 5/2001 |
| FR | 2846545 | 5/2004 |
| FR | 2935601 A1 | 3/2010 |
| GB | 140983 | 4/1920 |
| GB | 2119655 | 11/1983 |
| GB | 2227540 | 1/1990 |
| GB | 2336415 | 10/1999 |
| GB | 2430625 | 4/2007 |
| WO | 2006109004 | 10/2006 |
| WO | 2013/131974 A1 | 9/2013 |

OTHER PUBLICATIONS

Patent Examination Report issued for corresponding Australian patent application No. 2014224121, Aug. 11, 2016, 3 pages.

Office Action issued for corresponding Canadian patent application No. 2,864,697, Sep. 23, 2015, 3 pages.

English Translation of First Office Action issued for corresponding Chinese patent application No. 201410495357.1, Mar. 22, 2016, 6 pages.

European Search Report and European Search Opinion issued for corresponding European patent application No. 14187111.1, Feb. 6, 2015, 5 pages.

English Translation of the Second Office Action issued in connection with corresponding Chinese patent application No. 201410495357.1, Nov. 28, 2016, 7 pages.

* cited by examiner

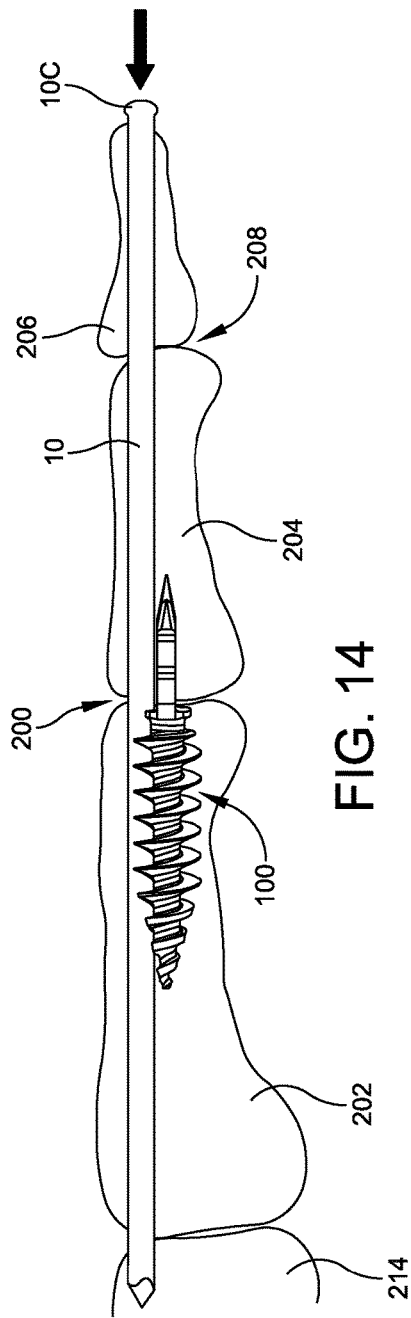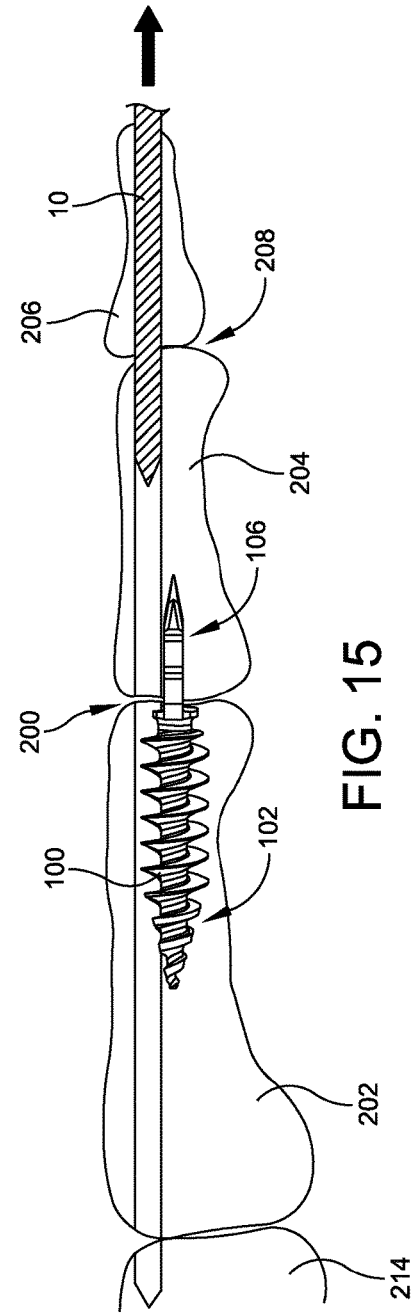

HAMMER TOE IMPLANT AND METHOD

FIELD OF DISCLOSURE

The disclosed system and method relate implants. More specifically, the disclosed system and method relate to installing an implant for treating hammer toe.

BACKGROUND

Hammer toe is a deformity of the toe that affects the alignment of the bones adjacent to the proximal interphalangeal (PIP) joint. Hammer toe can cause pain and can lead to difficulty in walking or wearing shoes. A hammer toe can often result in an open sore or wound on the foot. In some instances, surgery may be required to correct the deformity by fusing one or both of the PIP and distal interphalangeal (DIP) joints. Improved implants and surgical devices are desirable.

SUMMARY

In some embodiments, an implant includes an elongate threaded portion defining a first central longitudinal axis and a groove. The groove defines a second longitudinal central axis that extends in the same direction as the first central longitudinal axis. A blade portion extends from the elongate threaded portion and has a taper terminating at a point.

In some embodiments, a method includes forming an incision to gain access to a joint between first and second bones, flexing the first and second bones such that the first and second bones are disposed at an angle with respect to one another, and inserting a surgical device into a first end of the first bone until a trailing end of the surgical device is disposed adjacent to the first end of the first bone. A slot is formed in the first end of the first bone adjacent to a location at which the surgical device is received within the first bone, and a threaded portion of an implant is advanced into a first end of the second bone. The first bone is repositioned such that the slot formed in the first bone aligns with a blade portion of the implant that extends from the first end of the second bone. The first bone is forced into engagement with the blade portion of the implant, and the first surgical device is advanced across the joint and into engagement with a groove defined by the threaded portion of the implant.

A method includes inserting a leading end of a surgical device into an exposed first end of a first bone until a trailing end of the surgical device is disposed adjacent to the first end of the first bone. A threaded portion of an implant is advanced into an exposed first end of a second bone, and the first bone is repositioned such that a slot formed in the first bone adjacent to the surgical device aligns with a blade portion of the implant that extends from the first end of the second bone. The first bone is forced into engagement with a blade portion of the implant, and the trailing end of the surgical device is advanced across a joint between the first and second bones and into a groove defined by the threaded portion of the implant.

BRIEF DESCRIPTION OF THE DRAWINGS

These and other features and advantages of the present invention will be more fully disclosed in, or rendered obvious by the following detailed description of preferred embodiments, which are to be considered together with the accompanying drawings wherein like numbers refer to like parts and further wherein:

FIG. 14 illustrates the surgical device being advanced into bones and engaging a portion of the implant in accordance with some embodiments; and FIG. 15 illustrates the surgical device being removed from bone and its engagement with the implant in accordance with some embodiments.

DETAILED DESCRIPTION

Figure 1:
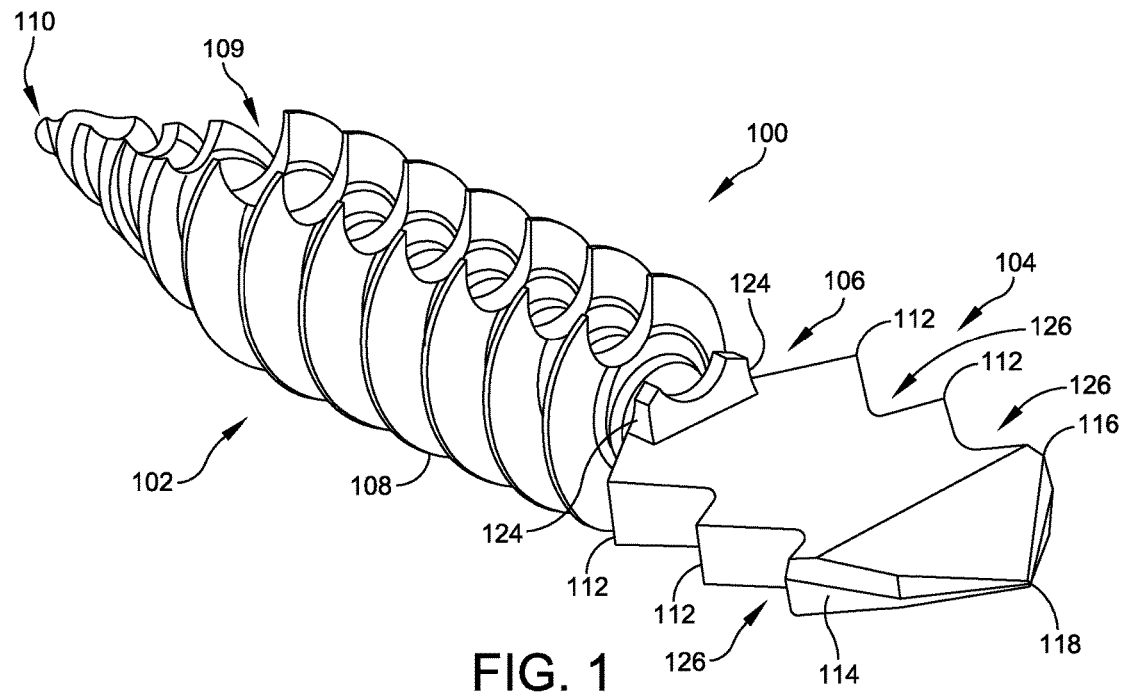
FIG. 1 is an isometric view of one example of an improved hammer toe implant in accordance with some embodiments.

This description of preferred embodiments is intended to be read in connection with the accompanying drawings, which are to be considered part of the entire written description. The drawing figures are not necessarily to scale and certain features of the invention may be shown exaggerated in scale or in somewhat schematic form in the interest of clarity and conciseness. In the description, relative terms such as "horizontal," "vertical," "up," "down," "top," and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral," and the like are to be interpreted relative to one another or relative to an axis of elongation, or an axis or center of rotation, as appropriate. Terms concerning attachments, coupling, and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship.

The disclosed implant, systems, and methods advantageously enable an implant to be installed through a small incision while stabilizing a joint, such as a metatarsophalangeal joint. Additionally, the implant is capable of being completely disposed within a toe of a patient, which prevents the implant from being caught on bed sheets or other objects like the conventional pins when installed for treating a joint condition.

Figure 2:
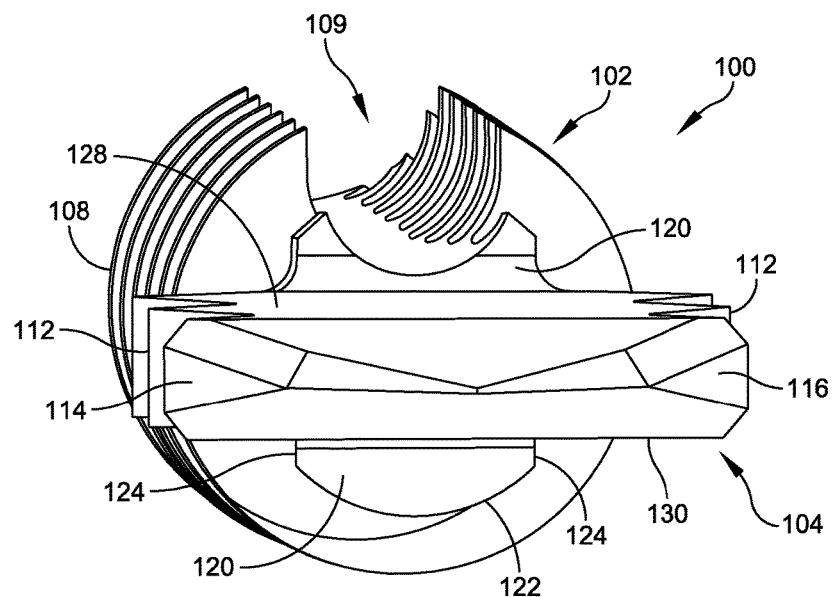
FIG. 2 is another isometric view of the hammer toe implant illustrated in FIG. 1 in accordance with some embodiments.

FIGS. 1-8 illustrate one example of an improved implant 100 for treating hammer toe in accordance with some embodiments. As best seen in FIGS. 1 and 2, implant 100 includes a threaded portion 102 and a blade portion 104, which are connected together at an engagement portion 106. Implant 100 may have a substantially linear geometry, such that a longitudinal axis defined by blade portion 104 is aligned or collinear with a longitudinal axis defined by threaded portion 102, and have an overall length of approximately 19 mm (approximately 0.75 inches). However, in some embodiments, blade portion 104 is disposed at angle with respect to a longitudinal axis defined by the threaded portion 102 such that a longitudinal axis defined by the blade portion 104 is not aligned nor collinear with a longitudinal axis defined by threaded portion 102. For example, in some embodiments, the angle is between zero and 45 degrees, and more particularly between approximately five and fifteen degrees. Commonly assigned U.S. patent application Ser. No. 13/086,136, filed Apr. 13, 2011 and which is incorporated by reference herein in its entirety, discloses one example of an implant having an angled (e.g., non-linear) configuration. One of ordinary skill in the art will understand that implant 100 may have other dimensions and be provided in different sizes. For example, implant 100 may be provided in lengths of 16 mm and 22 mm, to identify only a few potential lengths.

Threaded portion 102 includes a plurality of threads 108 disposed along its entire length. In some embodiments, the length of threaded portion 102 is approximately 13 mm (approximately 0.5 inches). Threaded portion 102 tapers to a pointed tip 110 to facilitate the advancement of threads 108 into bone. In some embodiments, threads 108 have a maximum outer diameter of approximately 2 mm (approximately 0.08 inches), although one skilled in the art will understand that thread portion 102 may have other dimensions and be configured to be received within a phalanx bone of a person. For example, in some embodiments, threads 108 have an outer diameter of between approximately 1.6 mm and 4 mm, such as, for example, 1.6 mm, 2.4 mm, 3.2 mm, and 4.0 mm, to identify only a few potential possibilities.

Figure 4:
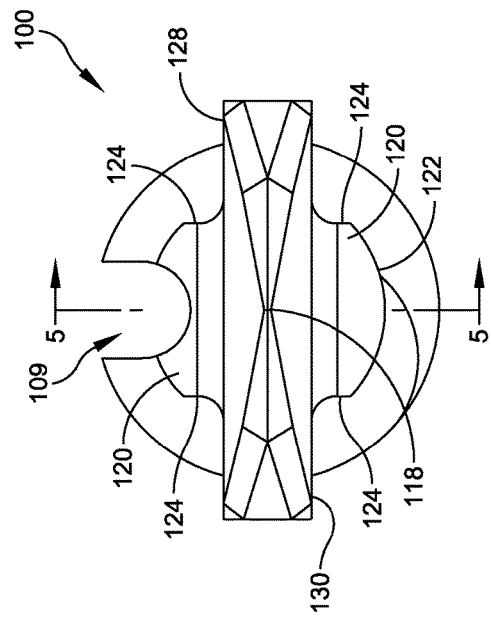
FIG. 4 is an end on view of the hammer toe implant illustrated in FIG. 1 in accordance with some embodiments.
Figure 6:
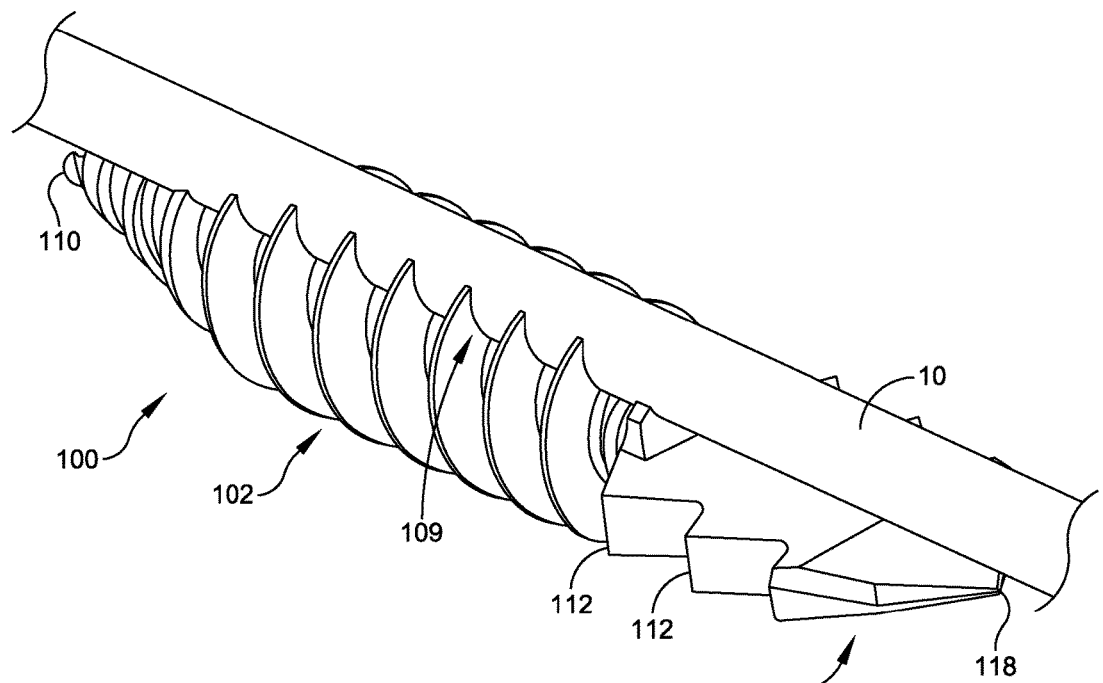
FIG. 6 is an isometric view of the hammer toe implant illustrated in FIG. 1 coupled to a surgical device in accordance with some embodiments.
Figure 7:
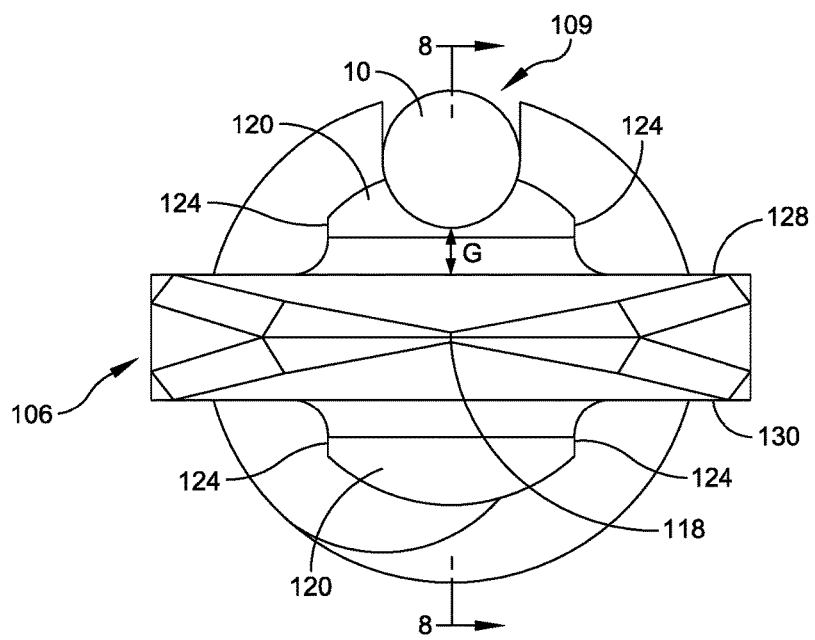
FIG. 7 is an end view of the hammer toe implant illustrated in FIG. 1 coupled to a surgical device in accordance with some embodiments.
Figure 8:
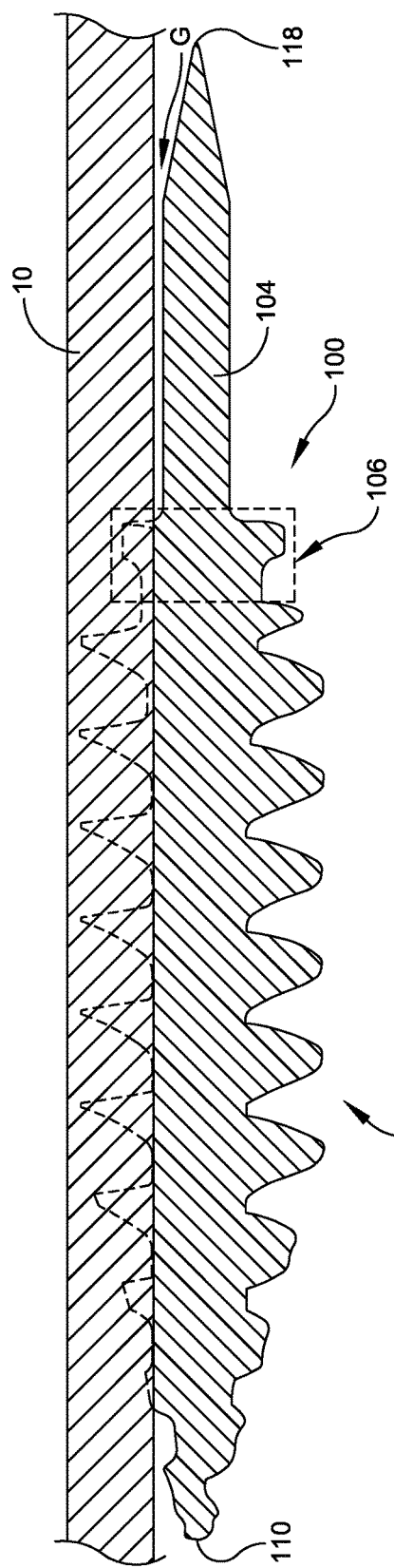
FIG. 8 is a cross-sectional view taken along line 8-8 in FIG. 7 of the hammer toe implant illustrated in FIG. 1 coupled to a surgical device in accordance with some embodiments.

Threaded portion 102 includes a groove 109 sized and configured to receive a k-wire, pin, or other surgical device or instrument therein as described in greater detail below. Groove 109 extend along the length of threaded portion 102 in a direction that is parallel to a longitudinal length defined by threaded portion 102. In some embodiments, as best seen in FIGS. 1 and 2, a central axis of groove 109 is disposed adjacent to a central longitudinal axis defined by threaded portion 102. Put another way, the central axis defined by groove 109 is not collinear with, and is parallel to, the central axis defined by threaded portion 102, which extends through the center of threaded portion 102 and blade portion 104. In some embodiments, groove 109 is disposed such that it is tangent to a minor diameter of threads 108. Although not shown, in some embodiments groove 109 is collinear with the central axis defined by threaded portion 102 (and blade portion 104). FIGS. 6 and 7 show a k-wire 10 disposed within groove 109. In some embodiments, such as the embodiment illustrated in FIG. 7, a gap G is provided between k-wire 10 and a side 128 of blade portion 104, which is disposed opposite of side 130 of blade portion 104 as shown in FIGS. 4 and 8. Gap G enables bone to be received between surgical device 10 and blade portion 104.

Figure 3:
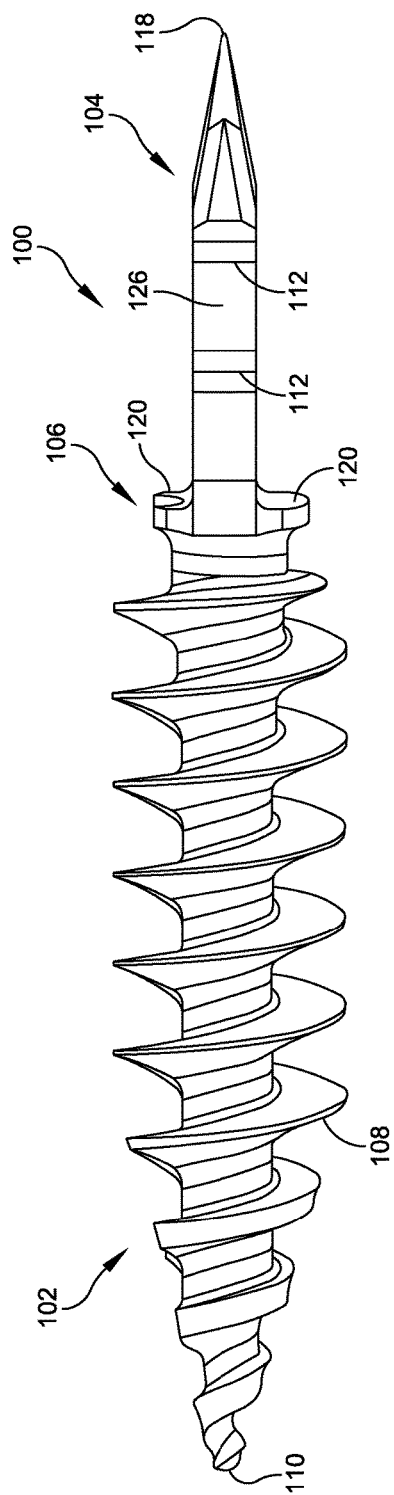
FIG. 3 is a side view of the hammer toe implant illustrated in FIG. 1 in accordance with some embodiments.

As best seen in FIG. 1, blade portion 104 includes a plurality of serrated edges 112 on first side 114 and on a second side 116. Serrated edges 112 each have a thickness that is approximately equal to the thickness of blade portion 104. Put another way, in some embodiments, blade portion 104 does not taper along its thickness direction as best seen in FIG. 3. Serrated edges are separated from one another by valleys or indentations 126 shown in FIGS. 1 and 3. Blade portion 104 may have a width that is greater than its thickness as best seen in FIGS. 1 and 2. For example, blade portion 104 may have a width of approximately 0.4 centimeters (approximately 0.16 inches) and a thickness of approximately 0.1 centimeters (approximately 0.04 inches) each of which taper to point 118 at the distal-most end of blade portion 104. In some embodiments, blade portion 104 has a substantially rectangular cross-sectional area as illustrated in FIG. 4, although one skilled in the art will understand that blade portion 104 may have other cross-sectional geometries.

Figure 5:
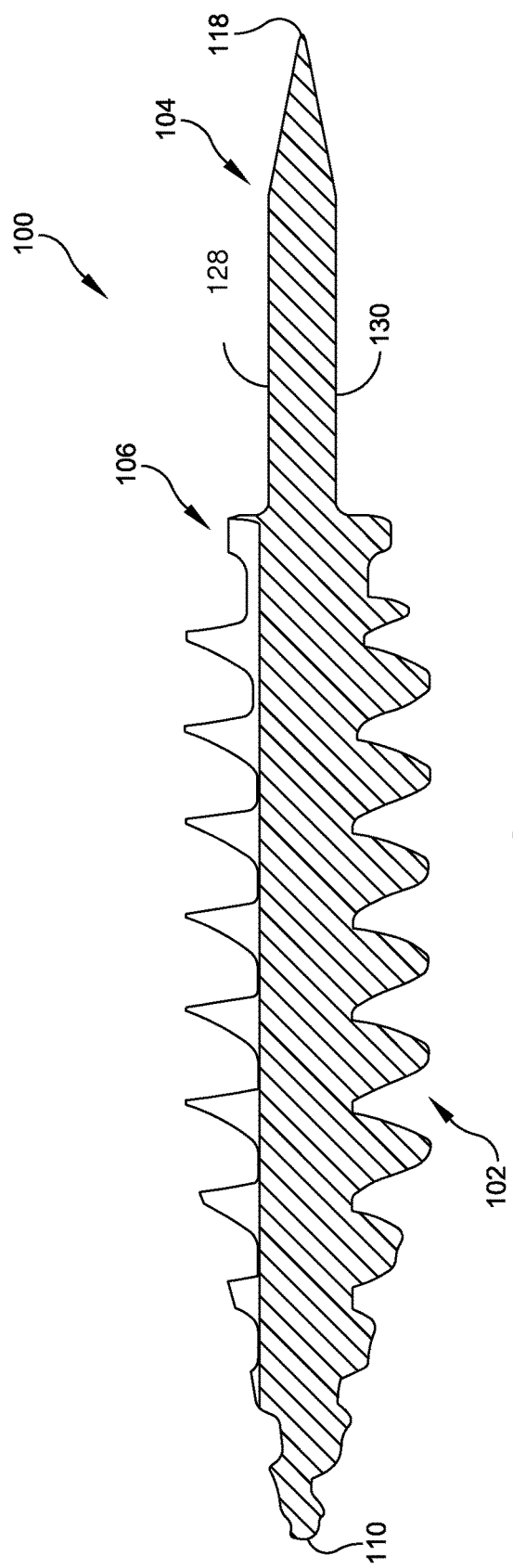
FIG. 5 is a sectional view of the hammer toe implant illustrated in FIG. 1 taken along line 5-5 in FIG. 4 in accordance with some embodiments.

Engagement portion 106 includes a pair of protrusions 120 extending from opposite sides of implant 100 and having rounded outer edges 122 as best seen in FIGS. 1 and 2. The sides 124 of protrusions 120 may be substantially parallel with each other as shown in FIG. 5. Protrusions extend away from one another in a direction that is perpendicular with respect to a longitudinal direction of implant 100.

Figure 10:
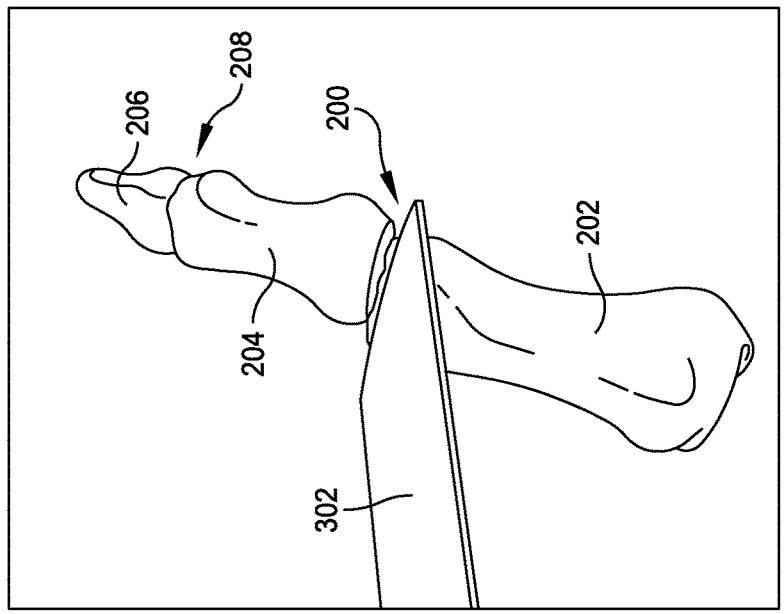
FIG. 10 illustrates one example of a cutting blade being used to resect faces of adjacent bones of a joint in accordance with some embodiments.
Figure 9:
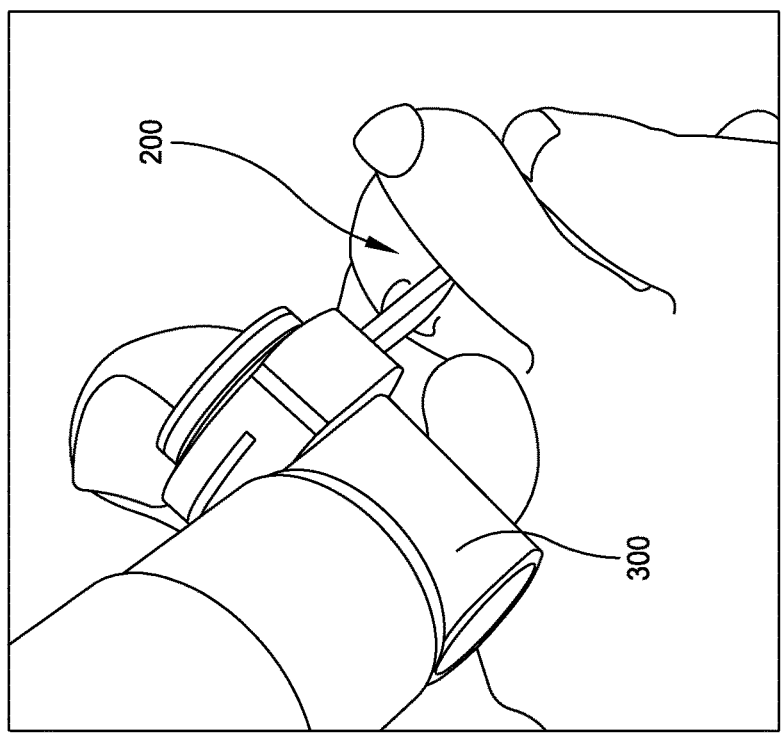
FIG. 9 illustrates one example of an incision being made to gain access to a joint between at least two bones in accordance with some embodiments.

A method of installing implant 100 in a joint between at least two bones is described with reference to FIGS. 9-15. Although the method is described as installing an implant in the bones of a proximal interphelangeal joint (PIP) 200, i.e., the joint between proximal phalange 202 and middle phalange 304, one of ordinary skill in the art will understand that the technique for installing the implant 100 may be applied to other joints, such as, for example, the distal interphelangeal (DIP) joint, i.e., joint 208 between middle phalange 304 and distal phalange 206. As shown in FIG. 9, an incision is made to open the PIP joint 200. In some embodiments, a cutting tool 300 having a blade 302 is used to resect adjacent faces of proximal phalanx 202 and middle phalanx 204 as shown in FIG. 10. The resected surfaces of proximal phalanx 202 and middle phalanx 204 may be debrided as understood by one of ordinary skill in the art.

Figure 11:
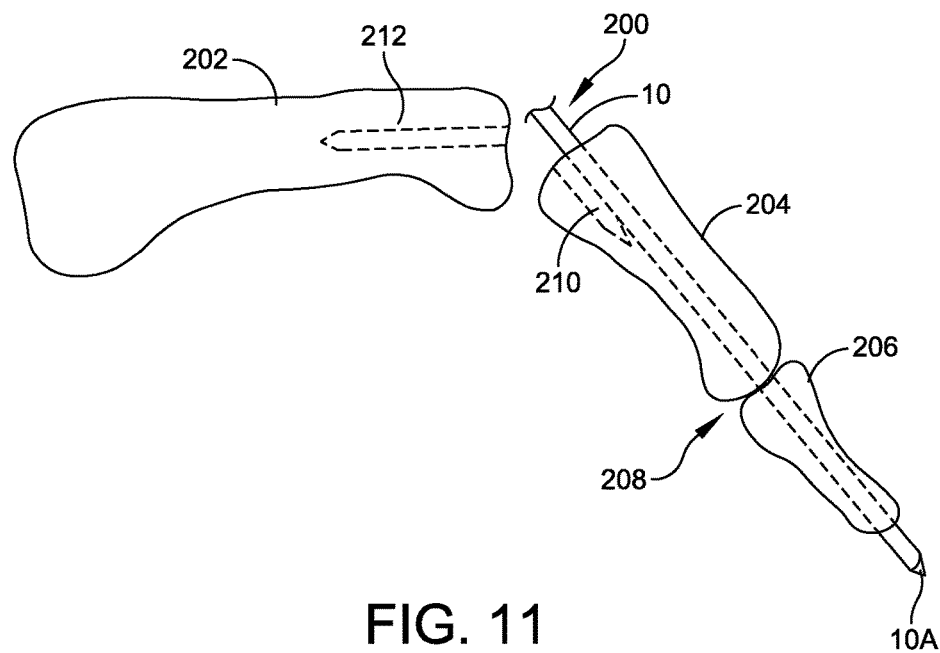
FIG. 11 illustrates a surgical device being inserted into a bone adjacent to a broach or drill site in accordance with some embodiments.

A k-wire, pin, or other suitable surgical device 10 is inserted into the middle phalange 204 and driven through distal phalange 206 and out the end of the toe as shown in FIG. 11. In some embodiments, middle phalange 204 is broached or pre-drilled to create an opening 210 also shown in FIG. 11, and a pilot hole 212 is formed in proximal phalange 202 using a drill, broach, or other suitable surgical device (not shown). The hole 210 created by the broach is located at a distance from the k-wire 10 that corresponds to the distance of gap G.

Figure 12:
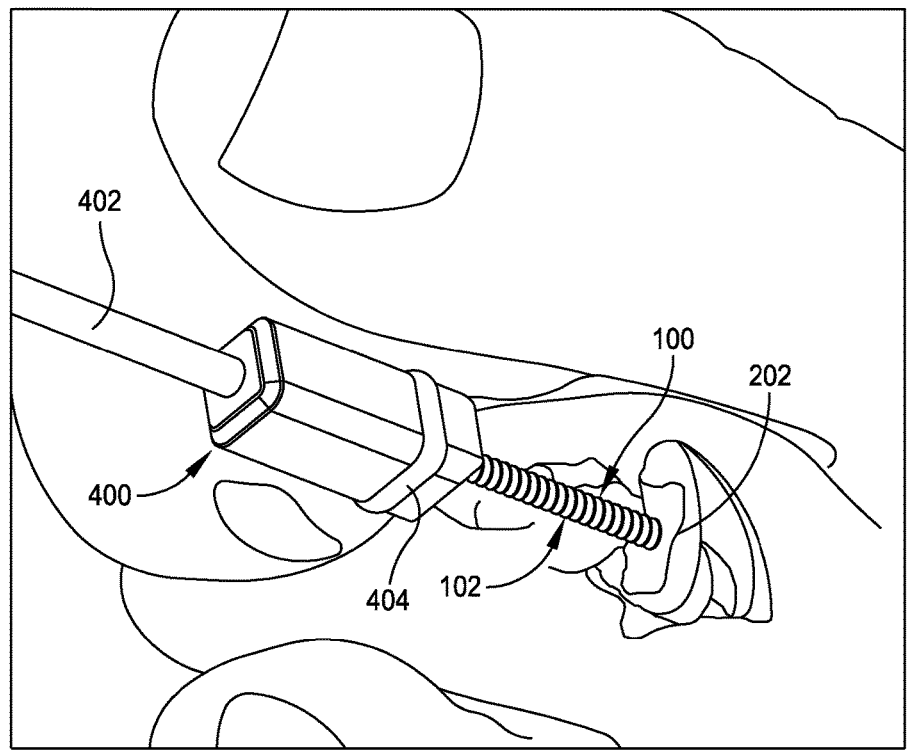
FIG. 12 illustrates one example of an implant being driven into a bone using a driving tool in accordance with some embodiments.

K-wire 10 is inserted such that trailing end 10B (not shown in FIG. 11) is disposed within middle phalange 204 or otherwise positioned with respect to joint 200 such that implant 100 can be driven into proximal phalange 202. In some embodiments, threaded portion 102 of implant 100 is driven into proximal phalange 202 using a driving tool. For example, FIG. 12 illustrates implant 100 being driven into middle phalange 204 using a driving tool 400, such as a driving tool disclosed in commonly assigned U.S. patent application Ser. No. 13/086,136, which is incorporated by reference herein in its entirety. One of ordinary skill in the art will understand that other driving tools can be used. Shaft 402 of driving tool 400 can be engaged with a chuck of a drill (not shown) to advance threaded portion 102 of implant 100 into pilot hole 212. Implant 100 is driven into bone until engagement portion abuts bone. Implant 100 is decoupled from driving tool 400 by axially pulling handle (not shown) away from implant 100 with sufficient force to flex o-ring 404 and separate driving tool 400 from implant 100.

Figure 13:
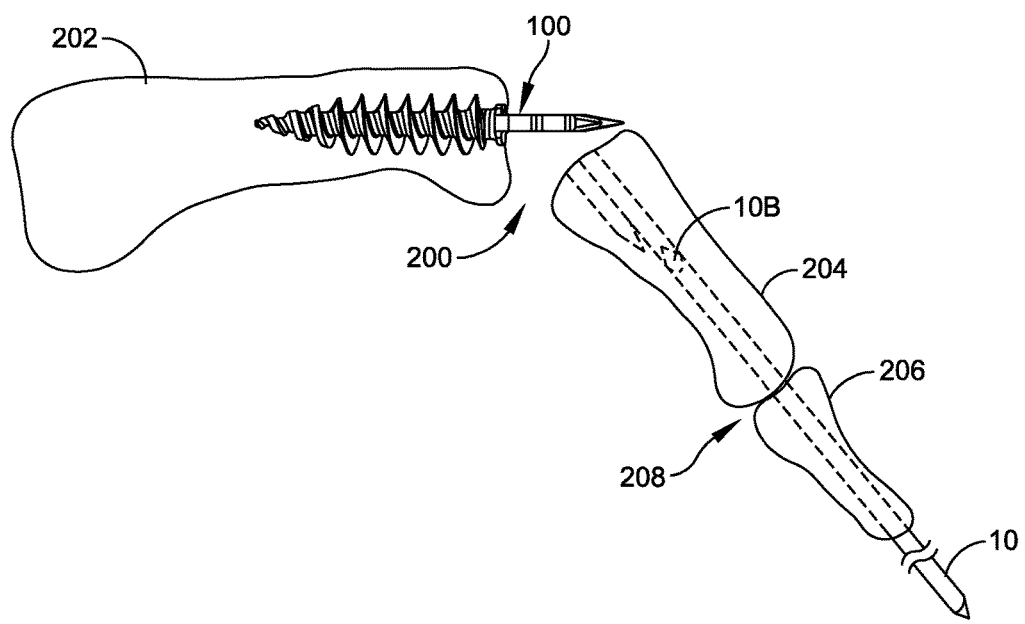
FIG. 13 illustrates an implant in accordance with FIG. 1 having been inserted into a bone disposed adjacent to the bone in which a surgical device is inserted in accordance with some embodiments.

FIG. 13 illustrates threaded portion 102 of implant 100 disposed within a first bone, such as proximal phalange 202, and end 10B of surgical device 10 disposed within a second bone, such as middle phalange 204. Blade portion 104 is exposed as it extends from the distal end of middle phalange 202.

The middle phalange 204 is repositioned such that hole 210 formed by broaching the middle phalange 204 aligns with the blade portion 104 of implant 100, which extends from the end of proximal phalange 202. Additionally, k-wire 10 disposed within middle phalange 204 aligns with the groove 109 defined by blade portion 104 of implant 100, which is disposed within proximal phalange 202. Middle phalange 204 is pressed into engagement with the blade portion 104 as shown in FIG. 14. Serrated edges 112 of blade portion 104 help to maintain the engagement between middle phalanx 204 and blade portion 104 of implant 100.

In some embodiments, k-wire 10 is advanced across joint 200, into and through middle phalange 202, and into metatarsal 214 through implant 100 as shown in FIG. 14. The k-wire 10 is received within groove 109 such that implant 100 engages surgical device 10. What was initially leading end 10A (FIGS. 11 and 13), can be blunted or capped to provide an exposed blunt end 10C shown in FIG. 14. The surgical device 10 can remain within a patient for a period of time, e.g., minutes, hours, days, or months, and then be removed as shown in FIG. 15 to leave behind implant 100.

Thus, in some embodiments a surgical method includes forming an incision to gain access to a joint between the first bone and the second bone, resecting at least one of the first end of the first bone and the first and of the second bone, and flexing the first bone relative to the second bone to expose the first end of the first bone and the first end of the second bone. A first surgical device is inserted into the first bone until a trailing end of the first surgical device disposed adjacent to a first end of the first bone. The first end of the first bone is broached at a location that is adjacent to a location at which the first surgical device is disposed in the first bone. A pilot hole is formed in the first end of the second bone, and a threaded portion of an implant is advanced into the pilot hole formed in the second bone. The first bone is repositioned such that the hole formed in the first end of the first bone by the broach is aligned with a blade portion of the implant extending from the first end of the second bone. The first bone is forced into engagement with the blade portion of the implant. The first surgical device is advanced across the joint, into the second bone such that first surgical device is received within a groove defined by the threaded portion of the implant. The first surgical device is further advanced across a second joint into a third bone. After a period of time, the first surgical device is removed from its engagement with the implant and the first, second, and third bones while the implant remains disposed within the first and second bones.

The implant described above may advantageously be installed through a small incision as described above. Further, the inclusion of a groove in the implant that is sized and configured to receive a k-wire enables the implant to be installed while the joint is stabilized.

Although the disclosed implant, system, and method have been described in terms of exemplary embodiments, they are not limited thereto. Rather, the appended claims should be construed broadly, to include other variants and embodiments of the system, implant, and method, which may be made by those skilled in the art without departing from the scope and range of equivalents of the implant, system, and method.

What is claimed is:

1. An implant system, comprising:
    an elongate threaded portion defining a first central longitudinal axis and a groove, the groove defining a second longitudinal central axis that extends in the same direction as the first central longitudinal axis;
    a blade portion extending from the elongate threaded portion, the blade portion having a taper terminating at a point;
    a first projection near a junction where the blade portion extends from the threaded portion, the first projection extending in a direction that is perpendicular to the first central longitudinal axis defined by the threaded portion, the first projection configured to abut bone when the implant is driven into the bone, the groove extending inward from an outermost edge of the first projection; and
    a k-wire seated in the groove, the k-wire extending along an entire length of the implant with a majority of the k-wire located radially past the outermost edge of the first projection, wherein the groove is configured to provide a gap between a first flat side of the blade portion and the k-wire inserted into the groove.

2. The implant system of claim 1, wherein the blade portion includes a plurality of serrated edges.

3. The implant system of claim 1, wherein the blade portion tapers along its width and thickness to the point.

4. The implant system of claim 1, further comprising an engagement portion disposed at the junction, the engagement portion including the first projection and a second projection extending in opposite directions away from each other in the direction that is perpendicular to the first central longitudinal axis defined by the threaded portion.

5. The implant system of claim 4, wherein the groove is further defined by one of the projections of the engagement portion.

6. The implant system of claim 1, wherein the second central longitudinal axis is disposed parallel to, but not collinear with, the first central longitudinal axis.

7. The implant system of claim 6, wherein the groove defined by the threaded portion is tangent to a minor diameter of the threads of the threaded portion.

8. The implant system of claim 1, wherein the first projection is configured to hold the k-wire with a majority of the k-wire located radially past the outermost edge of the first projection.

9. A method of using the implant system of claim 1, comprising:
    forming an incision to gain access to a joint between first and second bones;

flexing the first and second bones such that the first and second bones are disposed at an angle with respect to one another;

inserting a surgical device into a first end of the first bone until a trailing end of the surgical device is disposed adjacent to the first end of the first bone;

forming a slot in the first end of the first bone adjacent to a location at which the surgical device is received within the first bone;

advancing the threaded portion into a first end of the second bone;

repositioning the first bone such that the slot formed in the first bone aligns with the blade portion, and the blade portion extends from the first end of the second bone;

forcing the first bone into engagement with the blade portion; and advancing the first surgical device across the joint and into engagement with the groove defined by the threaded portion.

10. The method of claim 9, further comprising resecting at least one of the first end of the first and second bones prior to inserting the surgical device.

11. The method of claim 9, wherein the first bone is one of a proximal phalanx or a middle phalanx of a foot, and the second bone is the other of the proximal phalanx or the middle phalanx of a foot.

12. The method of claim 11, wherein the surgical device is further advanced across a second joint and into a metatarsal bone.

13. The method of claim 9, wherein the first central longitudinal axis is not collinear with the second central longitudinal axis.

14. The method of claim 9, further comprising forming a pilot hole in the first end of the second bone prior to advancing the threaded portion into the first end of the second bone.

15. A method of using the implant system of claim 1, comprising:

inserting a leading end of a surgical device into an exposed first end of a first bone until a trailing end of the surgical device is disposed adjacent to the first end of the first bone;

advancing the threaded portion into an exposed first end of a second bone;

repositioning the first bone such that a slot formed in the first bone adjacent to the surgical device aligns with the blade portion, and the blade portion extends from the first end of the second bone;

forcing the first bone into engagement with the blade portion; and advancing the trailing end of the surgical device across a joint between the first and second bones and into the groove defined by the threaded portion.

16. The method of claim 15, further comprising forming an incision to gain access to the joint between the first bone and the second bone;

flexing the first bone relative to the second bone to expose the first end of the first bone and the first end of the second bone; and resecting at least one of the first end of the first bone and the first and of the second bone.

17. The method of claim 16, further comprising forming a pilot hole in the first end of the second bone prior to advancing the threaded portion of the implant into the first end of the second bone.

18. The method of claim 16, further comprising advancing the surgical device across a second joint between the second bone and a third bone and into the third bone.

19. The method of claim 15, wherein the first central longitudinal axis is disposed parallel to, but not collinear with, the second central longitudinal axis.

\* \* \* \* \*